United States Patent [19]
Gollobin

[11] Patent Number: 5,789,443
[45] Date of Patent: Aug. 4, 1998

[54] METHOD FOR TREATING FLUSHING ASSOCIATED WITH MENOPAUSE

[76] Inventor: Charlotte Gollobin, 6710 Bradley Blvd., Bethesda, Md. 20817

[21] Appl. No.: 847,468

[22] Filed: Apr. 25, 1997

[51] Int. Cl.$^6$ ............................................... A61K 31/195
[52] U.S. Cl. ............................................................ 514/561
[58] Field of Search ............................................ 514/561

[56] References Cited

U.S. PATENT DOCUMENTS

| | | | |
|---|---|---|---|
| 3,608,075 | 9/1971 | Glen et al. | 424/238 |
| 3,733,407 | 5/1973 | Segre | 424/239 |
| 4,315,033 | 2/1982 | Lawrason | 424/319 |
| 4,421,744 | 12/1983 | Gormley | 424/177 |
| 4,687,781 | 8/1987 | Ehrenpreis et al. | 514/557 |
| 4,730,007 | 3/1988 | Ehrenpreis | 514/561 |
| 4,894,373 | 1/1990 | Young | 514/239.2 |
| 5,028,622 | 7/1991 | Plaitakis | 514/561 |
| 5,256,669 | 10/1993 | Askanazi et al. | 514/282 |
| 5,393,784 | 2/1995 | Richardson | 514/561 |

OTHER PUBLICATIONS

DiPalma et al., Annu. Rev. Nutr., "Use of Niacin as a Drug", 11:169–87 (1991).

Carpenter, K.J., *Experientia Suppl.*, "The Relationship of Pellagra to Corn and the Low Availability of Niacin in Cereals", 44:197–222, 1983. (Abstract).

Henderson, *Ann. Rev. Nutr.*, "Niacin", 3:289–307, 1983.

*Nutrition Reviews*, "Pellagragenic Effect of Excess Leucine", vol. 44, No. 1, Jan. 1986, pp. 26–27.

*Nutrition Reviews*, "Is Leucine Excess a Factor in Pellagra?", vol. 45, No. 10, Oct. 1987, pp. 313–315.

Harper et al., *Ann. Rev. Nutr.*, "Branched–Chain Amino Acid Metabolism", Ann. Rev. Nutr., pp. 432–439.

Jacob et al., *Present Knowledge in Nutrition*, "Niacin", pp. 163–169.

Rao et al., *Niacin*, Niacin, pp. 318–331.

*Primary Examiner*—Phyllis G. Spivack
*Attorney, Agent, or Firm*—Jacobson, Price, Holman & Stern, PLLC

[57] ABSTRACT

A method for treating flushing as a symptom of menopause is disclosed. Specifically, the method comprises administering to a patient in need thereof an effective amount of leucine, or leucine in combination with isoleucine and valine. Preferably the leucine is administered as a dietary supplement. However, treatment may be achieved via manipulation of dietary protein intake. Due to the depletion effect that leucine has on other branched chain amino acids, it is preferred that isoleucine and valine are administered in combination with leucine.

14 Claims, No Drawings

METHOD FOR TREATING FLUSHING ASSOCIATED WITH MENOPAUSE

FIELD OF THE INVENTION

This invention is directed to a method for treating symptoms of menopause, such as hot flashes (flushing) and the like. Specifically, this invention is directed to administering, to a female patient, an effective amount of branched chain amino acids, specifically leucine. Leucine may be administered by manipulation of diet or in a composition comprising an effective amount of leucine and a pharmaceutically acceptable carrier. A combination of leucine, isoleucine and valine is preferred.

BACKGROUND OF THE INVENTION

Menopausal syndrome consists of a number of varying and often highly distressing symptoms resulting from hormonal imbalance in the female body, specifically a deficiency of estrogen in the body. Symptoms of menopausal syndrome sufficiently severe to require treatment occur in approximately 50 percent of women. One particular symptom experienced by women is hot flashes or flushing. This is characterized by a sudden onset of warmth in the face and neck and often progressing to the chest. Such an episode generally lasts several minutes and is evidenced by a visible red flushing of the skin. Often such episodes are accompanied by sweating, dizziness, nausea, palpitations and diaphoresis.

Estrogen replacement therapy provides relief to 90% of women who experience such menopausal symptoms and has, over the years, become increasingly popular. U.S. Pat. No. 3,608,075, to Glen et al. discloses the Use of an orally active estrogen in the treatment of menopausal syndrome. In particular, a composition containing sodium 17 beta-dihydroequilin sulfate as the sole estrogenic agent for the treatment of menopausal syndrome in women is disclosed. An example of the use of a graded sequential estrogen-progestogen regime is disclosed in U.S. Pat. No. 3,733,407 to Segre.

While estrogen therapy is thought to be successful in alleviating symptoms, it is not without side effects. In some cases, the side effects can be quite severe. Such side effects include an increased risk of certain cancers, for example, breast cancer. Estrogen has also been implicated in certain endoimetrial cancers. Although treatments with progestin have been shown to counter these adverse side effects, postmenopausal women treated with such estrogen-progestin regime& frequently experience undesirable uterine bleeding. Clearly, there is a need for an alternative to estrogen therapy for hot flashes or flushing and the like in menopausal women.

In U.S. Pat. No. 4,894,373 to Young, the use of "true" antiestrogens, for example, clomiphene, zuclomiphene, enclomiphene, and citrates thereof, are disclosed as an alternative to estrogen for the treatment of menopausal symptoms. U.S. Pat. No. 4,315,033 to Lawrason discloses the use of methyldopa for treating vasomotor-instability associated with menopausal syndrome.

Another alternative to estrogen therapy has been disclosed in U.S. Pat. No. 4,421,744 to Gormley. In this patent, the use of peptide or pseudo peptide derivative compounds of the following formula are disclosed:

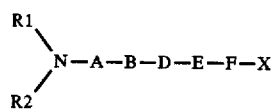

wherein R1 and R2 are hydrocarbyl or halo-hydrocarbyl substituents, for example alk-2-enyl radicals; >N-A- is a defined amino acid residue; B, D and E, which may be the same and different, are a valency bond or a defined amino acid residue; F is a defined amino acid residue; X is a carboxy, ester or amide group; and the linkages between the amino acid residues are peptide linkages or at least one of the linkages is a pseudo linkage. Such compounds are active antagonists at the so called opiate receptors, in warm blooded mammals, and are therefore useful in the treatment of a number of conditions and/or diseases, including disorders of the endocrine function, such as post-menopausal flushing.

There is, however, no mention in any of the above referenced patents to the use of leucine as an alternative to estrogen therapy for the treatment of menopausal symptoms, such as hot flashes and the like.

Leucine is an amino acid which is thought to be associated with pellagra, a disease which results from a deficiency in niacin. It has been found that black tongue in dogs and niacin deficiency in monkeys can be induced by feeding a diet which contains high levels of leucine. Also, niacin deficiency can be induced by supplementing a non-pellagragenic diet with leucine. Results of several biochemical studies have indicated that excess leucine in the diet brings about a conditioned niacin deficiency by acting on the tryptophan-niacin biochemical pathway. It has been suggested that leucine acts by inhibiting the key rate limiting enzyme, namely quinolinate phosphorybosyltransferase, and also by increasing the activity of picolinate carboxylase, a key enzyme in the degradation of tryptophan. (Present Knowledge in Nutrition, 5th Edition, (1984), chapter 22, pp. 318–331).

Other studies suggest that leucine acts by altering kynurenase activity, an intermediate in the biochemical conversion pathway and by increasing the activity of hepatic NAD(P) glycohydrolase. Other studies suggest that leucine may act by impairing the cellular uptake of tryptophan. (Jacob, R. A. and Swenseid, M. E., Present Knowledge in Nutrition, 6th Edition, Washington, D.C., (1990); Bender, D. A., Effects of Dietary Excess of Leucine on Metabolism of Tryptophan in the Rat; a mechanism for pellagragenic action of leucine, Br. J. Nutr., (1983), vol. 50(1):pp.25–32).

It has also been suggested that estrogen may inhibit niacin production via the tryptophan-niacin biochemical pathway. (Bender, D. A. and Totoe, L., Inhibition of Tryptophan Metabolism by Oestrogens in the Rat: A Factor in the Aetiology of Pellagra, Br. J. of Nutr. (1984), vol 51:pp.219–224). In this study, it was suggested that when diet is only marginally adequate in tryptophan and niacin, inhibition of tryptophan metabolism by endogenous or administered estrogen may be an additional factor in the development of pellagra.

At menopause, and during the peri-menopausal interval, estrogen levels in women decrease. As mentioned above, one of the menopausal symptoms experienced by many women is flushing. Studies have shown that large doses of niacin can cause flushing when prescribed to lower serum cholesterol levels. (Altchul et al., Influences of Nicotinic Acid on Serum Cholesterol Levels in Man, Arch. Biochem. Biophys. (1955), vol. 54: pp. 558–559 and Morrow et al.

Identification of Skin as Major Site of PDG2 Release Following Oral Administration of Niacin in Humans, *J. Invest. Dermatol.* (1992), vol 98(5): pp.812–815). Flushing was observed as a side effect of high doses of nicotinic acid (DiPalma, J. R. and Thayer, W. S., Use of Niacin as a Drug, *Ann. Rev. Nutr.* (1991), vol 11: pp. 169–187 and Henderson, L. M. Niacin, *Ann. Rev. Nutr.* (1983) vol 3: pp. 289–307), and intense flushing has been observed following ingestion of pharmacological doses of niacin (Morrow et al., Release of Markedly Increased Quantities of PGD2 in vivo Following Administration of Nicotinic Acid, *Prostaglandin* (1989), vol. 38(2):pp. 263–274).

Leucine has been previously used in compositions for the treatment of pain, as an analgesic and anti-inflammatory. In U.S. Pat. No. 5,256,669 to Askanazi et al., the disclosure of which is expressly incorporated herein by reference, the use of an analgesic solution comprising at least one branched chain amino acid selected from the group consisting of leucine, isoleucine and valine is disclosed. In U.S. Pat. Nos. 4,730,007 and 4,687,781 to Ehrenpreis and Ehrenpreis et al., respectively, both disclosures of which are expressly incorporated herein by reference, analgesic and anti-inflammatory compositions which include D-leucine and DL-leucine are disclosed.

Other known uses for leucine include the treatment of neurodegenerative disorders, as disclosed in U.S. Pat. No. 5,028,622 to Plaitakis, the treatment of addiction to narcotic drugs as disclosed in U.S. Pat. No. 5,256,669 to Askanazi et al., also mentioned above, and the treatment of psychiatric disorders as disclosed in U.S. Pat. No. 5,393,784 to Richardson. The disclosures in the above patents to Plaitakis and Richardson are expressly incorporated herein by reference.

However, prior to the present invention, the use of leucine either alone or in combination with other branched chain amino acids has not been reported or suggested for the treatment of menopausal symptoms, such as flushing and the like.

SUMMARY OF THE INVENTION

Therefore, it is the object of the present invention to provide a method for reducing and eliminating menopausal symptoms, such as flushing and the like, in menopausal and peri-menopausal females, both safely and effectively, without the need for hormone replacement therapy and other therapies which are not without dangerous and costly side effects.

The present invention provides a method for the treatment of menopausal symptoms, such as flushing and the like, by administering to a female patient suffering from such symptoms, a therapeutically effective amount of leucine. Preferably, leucine is administered to the patient orally, in combination with isoleucine and valine.

The present invention also provides a method for treatment of flushing and similar symptoms in menopausal and peri-menopausal females. The method comprises administering to the female patient, a composition comprising leucine together with a pharmaceutically acceptable carrier.

The present invention further provides a method for treating flushing and the like in menopausal and peri-menopausal females which comprises administering to a female patient in need thereof a composition comprising an effective amount of leucine, isoleucine, and valine, together with a pharmaceutically acceptable carrier.

DESCRIPTION OF PREFERRED EMBODIMENTS

It is to be understood that while specific embodiments of the present invention are described herein, the invention is not to be limited to such embodiments, and that the present invention is directed to the surprising discovery that leucine and/or leucine in combination with isoleucine and valine, are effective in the treatment of menopausal symptoms, such as flushing and the like.

The branched chain amino acids of the present invention include leucine, isoleucine and valine. The most preferred forms of these branched chain amino acids include L-leucine, L-isoleucine and L-valine. Due to the depression effect that high intakes of leucine may have on other amino acids in the body, such as valine and isoleucine, it is preferred that isoleucine and valine be administered together with leucine, either as part of the composition or via an alternative route.

The branched chain amino acids according to the present invention may be administered in any form. Further, although any route of administration may be used, the preferred route of administration is orally. Examples of oral forms include both solid and liquid dosage forms, specifically capsules, tablets, dietary supplements, powders, solutions, syrups, elixirs and the like. The branched chain amino acids can also be orally administered by manipulation of dietary protein intake.

The therapeutically effective amounts of branched chain amino acids administered is to be an amount sufficient to effectively reduce and/or eliminate flushing and will vary according to the mode of administration and the weight of the patient. Such an effective amount would be easily discernable to a person of ordinary skill in the art. See for example, *Remington's Pharmaceutical Sciences*, Eighteenth edition, 1990, the disclosure of which is expressly incorporated herein by reference.

The preferred amount of leucine to be administered to the patient is between 250–1000 mg/day, more preferably between 400–700 mg/day. The preferred amount of isoleucine is between 150–700 mg/day, more preferably between 200–500 mg/day. The preferred amount of valine is between 100–600 mg/day, more preferably between 200–400 mg/day. Other compounds may be administered simultaneously with the amino acids, especially where the amino acid is administered in the form of a dietary supplement. Examples of such compounds include vitamins, particularly vitamin B6, and minerals, particularly calcium.

Pharmaceutically acceptable carriers, excipients and diluents include those which are well known in the art. Examples of such carriers, diluents and excipients include starch, sugars, talc and the like. Other agents well known in the art may also be included in compositions of the present invention. Examples of such agents include adjuvants, wetting agents, emulsifying agents, and sweetening agents.

EXAMPLE 1

A woman in peri-menopausal state and whose relevant medical history included hot flashes and profuse sweating such that at times three changes of clothes per day were required, and which hot flushes and sweating had persisted over a period of about 3 years, was treated as follows.

Two gel capsules which contain a total of 540 mg L-leucine, 360 mg L-isoleucine, 300 mg L-valine and 20 mg vitamin B-6 were taken daily via oral route. Such a formulation is available over the counter as a dietary supplement. Such a formulation is sold under the name of SOLGAR, manufactured by Solgar Pharmaceuticals Ltd.

Hot flushing and sweats were experienced for about 2½ weeks after commencement of treatment. On about day 21, total subsidence of the hot flushes and sweats was achieved.

Symptoms returned when the treatment was missed or stopped, but upon resuming treatment, as above, flushing and sweats again subsided. The only time an increase in body temperature was encountered was when the patient ate or drank hot food or drink. The above treatment continued to be effective over a period lasting approximately 1 year, and continues to do so.

The foregoing examples and description should be considered as illustrative of the principles of the invention. Since modifications and improvements of the present invention may occur to those skilled in the art, it is not intended to limit the invention to the specific examples disclosed. Rather, all suitable modifications and equivalents may be resorted to, falling within the scope of the invention.

What is claimed is:

1. A method for treating flushing as a symptom of menopause and symptoms which accompany such flushing which comprises administering to a patient in need thereof, a therapeutically effective amount of leucine.

2. The method of claim 1 wherein leucine is administered by manipulation of diet.

3. The method of claim 1 wherein leucine is administered in combination with therapeutically effective amounts of isoleucine and valine.

4. The method of claim 3 wherein the combination comprises L-leucine, L-isoleucine and L-valine.

5. The method of claim 3 wherein the therapeutically effective amount of isoleucine is between 150–700 mg/day.

6. The method of claim 3 wherein the therapeutically effective amount of valine is between 100–600 mg/day.

7. The method of claim 3 wherein the therapeutically effective amount of isoleucine is between 200–500 mg/day.

8. The method of claim 3 wherein the therapeutically effective amount of valine is between 200–400 mg/day.

9. The method of claim 1 wherein leucine is administered in a composition further comprising a pharmaceutically acceptable carrier, diluent or excipient.

10. The method of claim 9 wherein the composition administered is in the form of a gel capsule.

11. The method of claim 10 wherein two gel capsules are administered daily and the two gel capsules comprise approximately 540 mg of L-leucine, approximately 360 mg L-isoleucine and approximately 300 mg L-valine.

12. The method of claim 9 wherein the composition further comprises vitamin B-6.

13. The method of claim 1 wherein the therapeutically effective amount of leucine is between 250–1000 mg/day.

14. The method of claim 1 wherein the therapeutically effective amount of leucine is between 400–700 mg/day.

* * * * *